(12) United States Patent
Deister et al.

(10) Patent No.: US 12,285,299 B2
(45) Date of Patent: Apr. 29, 2025

(54) DEVICES AND METHODS FOR PROTECTING AGAINST NEUROMAS

(71) Applicant: AXOGEN CORPORATION, Alachua, FL (US)

(72) Inventors: Curt Deister, Alachua, FL (US); Crystal Simon, Alachua, FL (US); Jennifer Faleris, Alachua, FL (US)

(73) Assignee: Axogen Corporation, Alachua, FL (US)

( * ) Notice: Subject to any disclaimer, the term of this patent is extended or adjusted under 35 U.S.C. 154(b) by 857 days.

(21) Appl. No.: 17/509,178

(22) Filed: Oct. 25, 2021

(65) Prior Publication Data

US 2022/0104904 A1 Apr. 7, 2022

Related U.S. Application Data

(63) Continuation of application No. 17/172,886, filed on Feb. 10, 2021, which is a continuation of application
(Continued)

(51) Int. Cl.
*A61L 31/14* (2006.01)
*A61B 90/00* (2016.01)
(Continued)

(52) U.S. Cl.
CPC .............. *A61B 90/08* (2016.02); *A61L 31/14* (2013.01); *A61N 1/0558* (2013.01);
(Continued)

(58) Field of Classification Search
None
See application file for complete search history.

(56) References Cited

U.S. PATENT DOCUMENTS

| 4,778,467 A | 10/1988 | Stensaas et al. |
| 5,705,178 A | 1/1998 | Roufa et al. |

(Continued)

FOREIGN PATENT DOCUMENTS

| WO | 2012097297 A1 | 7/2012 |
| WO | 2014130419 A1 | 8/2014 |
| WO | 2016144166 A1 | 9/2016 |

OTHER PUBLICATIONS

Curtin et al., "Cutaneous Neuroma Physiology and Its Relationship to Chronic Pain", J. Hand Surg Am., vol. 34, 2009, pp. 1334-1336, XP026581520, DOI: 10.1016/j.jhsa.2009.04.003.
(Continued)

*Primary Examiner* — Rebecca S Preston
(74) *Attorney, Agent, or Firm* — Bookoff McAndrews, PLLC

(57) ABSTRACT

The subject invention provides devices and methods for alleviating discomfort associated with neuroma formation. The devices and methods of the invention effectively use the body's natural response of reconstructing implanted biomaterials to minimize the size of, isolate, and protect a neuroma. In preferred embodiments, the subject device is a cylindrical cap, wherein the internal chamber of the cylindrical cap physically partitions the nerve to enable an arrangement of nerve fibers (as opposed to haphazardly arranged nerve fibers often produced in neuromas). Tabs arranged on the outside of the cap can be used to manipulate the cap into place on a nerve. The open end can also be configured with flaps that can be used to widen the open end for easier insertion of the nerve into the cap. In addition, the cap's material remodels into a tissue cushion after implantation, which protects the neuroma from being stimulated and inducing pain.

30 Claims, 9 Drawing Sheets

Related U.S. Application Data

No. 15/496,578, filed on Apr. 25, 2017, now Pat. No. 10,952,806, which is a continuation-in-part of application No. 14/036,405, filed on Sep. 25, 2013, now Pat. No. 9,629,997.

(60) Provisional application No. 61/705,251, filed on Sep. 25, 2012.

(51) Int. Cl.
*A61N 1/05* (2006.01)
*A61L 27/36* (2006.01)
*A61L 31/00* (2006.01)
*A61L 31/04* (2006.01)
*A61L 31/06* (2006.01)

(52) U.S. Cl.
CPC ... *A61B 2090/0815* (2016.02); *A61L 27/3675* (2013.01); *A61L 31/005* (2013.01); *A61L 31/04* (2013.01); *A61L 31/048* (2013.01); *A61L 31/06* (2013.01); *A61L 2430/32* (2013.01); *A61N 1/05* (2013.01)

(56) References Cited

U.S. PATENT DOCUMENTS

| | | | |
|---|---|---|---|
| 6,225,079 | B1* | 5/2001 | Muller .................. B01L 3/502 |
| | | | 435/29 |
| 7,918,897 | B2 | 4/2011 | Bertram et al. |
| 9,352,146 | B2 | 5/2016 | Langhals et al. |
| 2006/0100647 | A1* | 5/2006 | Doi ........................ A61L 27/58 |
| | | | 606/152 |
| 2006/0224242 | A1 | 10/2006 | Swords et al. |
| 2007/0276507 | A1 | 11/2007 | Bertram et al. |
| 2010/0055149 | A1 | 3/2010 | Li et al. |
| 2013/0304174 | A1 | 11/2013 | Langhals et al. |
| 2014/0094932 | A1 | 4/2014 | Deister et al. |
| 2018/0339083 | A1* | 11/2018 | van den Berg ..... A61L 27/3878 |

OTHER PUBLICATIONS

Nordin et al., "Ectopic Sensory Discharges and Paresthesia in Patients with Disorders of Peripheral Nerves, Dorsal Roots and Dorsal Columns", PAIN, vol. 20, 1984, pp. 231-245, XP024377363, DOI: 10.1016/0304-3959(84) 90013-7.

Scadding, "Development of Ongoing Activity, Mechanosensitivity, and Adrenaline Sensitivity in Severed Peripheral Nerve Axons", Exp Neurol., vol. 73, 1981, pp. 345-364, XP026226365, DOI: 10.1016/0014-4886(81)90271-5.

Wall et al., "Ongoing Activity in Peripheral Nerves: The Physiology and Pharmacology of Impulses Originating from a Neuroma", Exp Neurol., vol. 43, 1974, pp. 580-593, XP026247081, DOI: 10.1016/0014-4886(74)90197-6.

Mackinnon et al., "Alteration of Neuroma Formation by Manipulation of Its Microenvironment", Plast Reconstr Surg., vol. 76, 1985, pp. 345-353.

PCT International Search Report and Written Opinion issued in International Application No. PCT/US2018/029305, dated Sep. 4, 2018.

Ducic, I. et al. "The Role of Peripheral Nerve Surgery in the Treatment of Chronic Pain Associated with Stumps." Plastic Reconstructive Surgery, Mar. 2008, 121(3):908-914 doi: 10-1097/01.prs.0000299281.57480.77.

Lewin-Kowalik, J. et al. "Prevention and Management of Painful Neuroma." Neurologia Medico-Chirurgica, Feb. 2006, 46(2): 62-68, doi: 10.2176/nmc.46.62.

Rajput, K. et al. "Painful Neuromas: A Review." Clinical Journal of Pain, Sep. 2012, 28(7): 639-645, doi: 10.1097/AJP.0b013e31823d30a2.

Stokvis, A. et al. "Surgical Management of Neuroma Pain: A Prospective Follow-Up Study." Pain, Dec. 2010, 151(3):862-869, doi: 101016/j-pain.2010.09.032.

\* cited by examiner

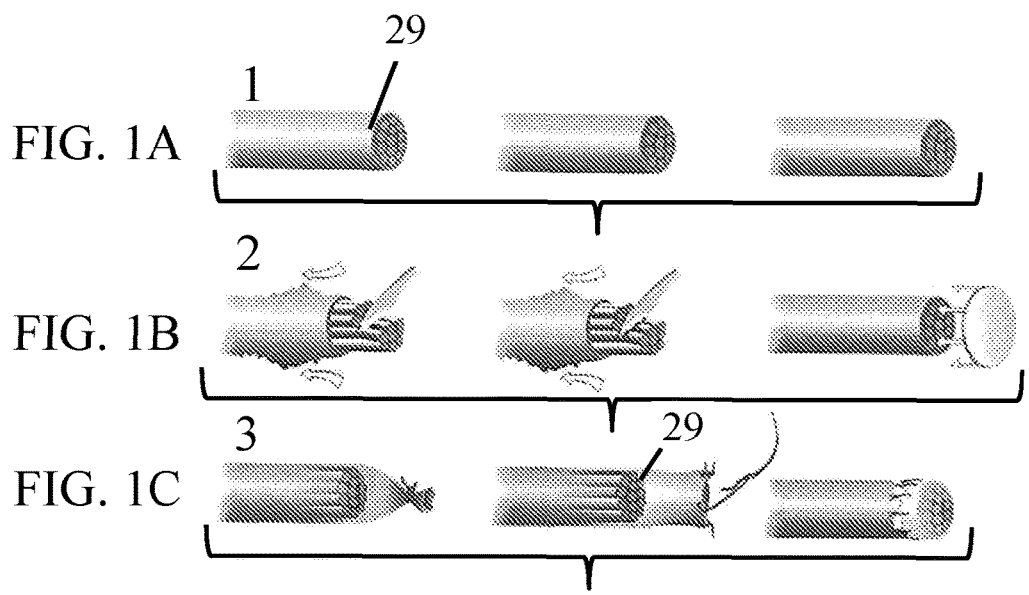
FIG. 1A
FIG. 1B
FIG. 1C
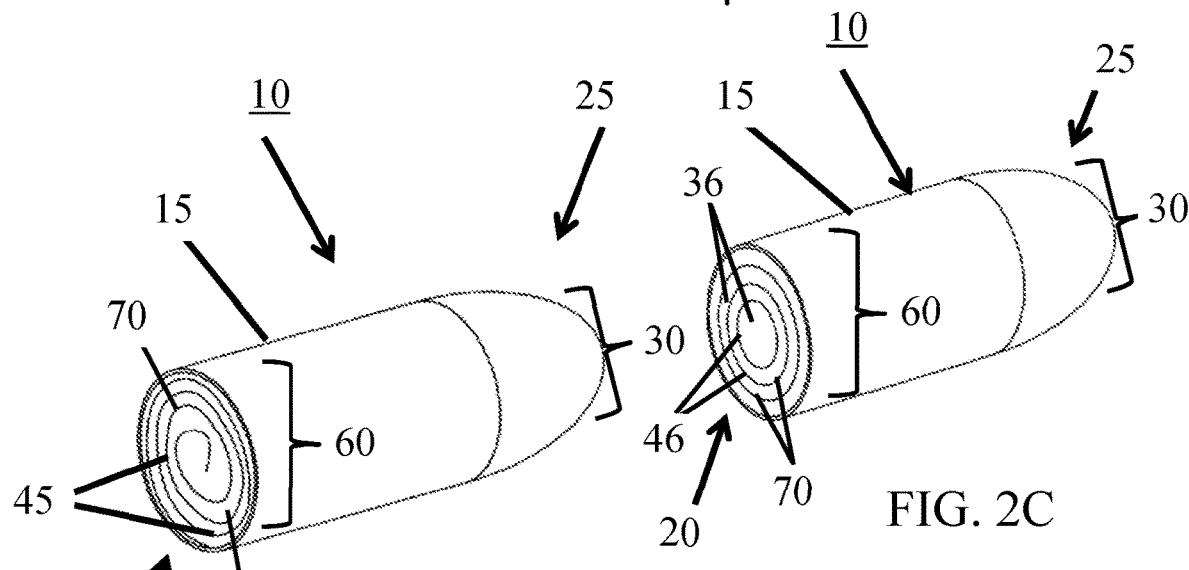
FIG. 2A
FIG. 2C
FIG. 2B

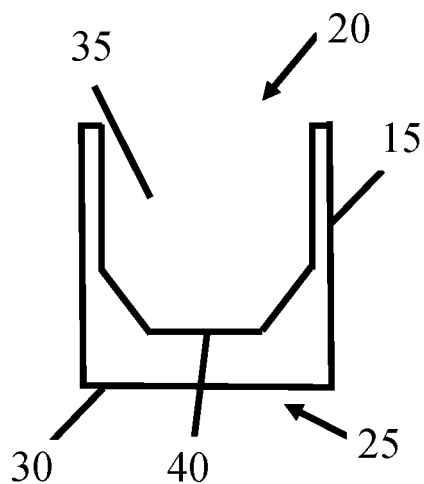
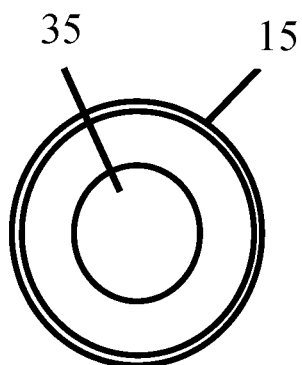
FIG. 3A  FIG. 3B
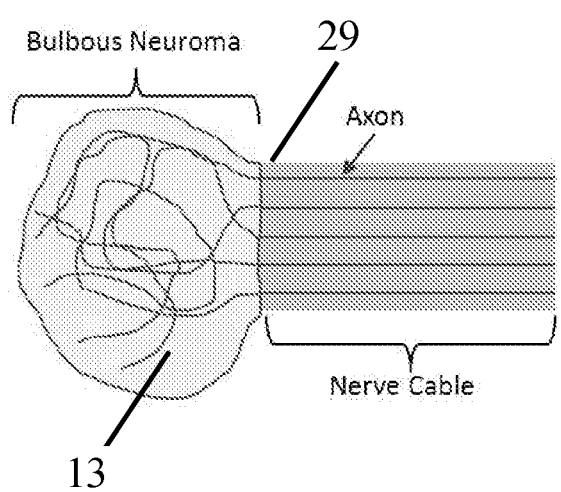
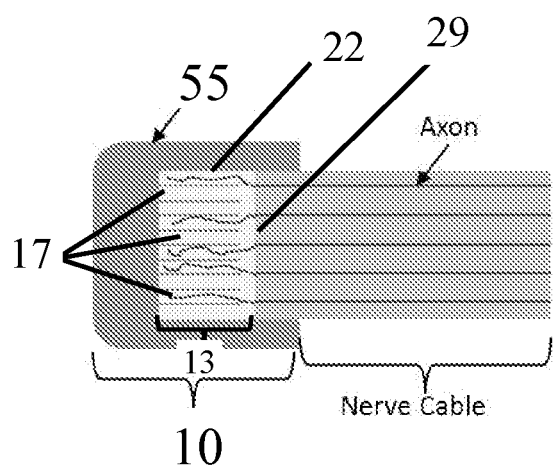
FIG. 4A  FIG. 4B

DEVICES AND METHODS FOR PROTECTING AGAINST NEUROMAS

CROSS-REFERENCE TO RELATED APPLICATIONS

This patent application is a continuation of and claims the benefit of priority to U.S. Nonprovisional patent application Ser. No. 17/172,886, filed on Feb. 10, 2021, which is a continuation of Nonprovisional patent application Ser. No. 15/496,578, filed on Apr. 25, 2017, which issued as U.S. Pat. No. 10,952,806, on Mar. 23, 2021, and which is a continuation-in-part of U.S. Nonprovisional patent application Ser. No. 14/036,405, filed on Sep. 25, 2013, which issued as U.S. Pat. No. 9,629,997, on Apr. 25, 2017, and which claims the benefit of priority to U.S. Provisional Patent Application No. 61/705,251, filed on Sep. 25, 2012, each of which is incorporated herein by reference in its entirety.

BACKGROUND OF INVENTION

Neuromas develop as a part of a normal reparative process following peripheral nerve injury. They are formed when nerve recovery towards the distal nerve end or target organ fails and nerve fibers improperly and irregularly regenerate into the surrounding scar tissue. Neuromas consist of a deranged architecture of tangled axons, Schwann cells, endoneurial cells, and perineurial cells in a dense collagenous matrix with surrounding fibroblasts (Mackinnon S E et al. 1985. Alteration of neuroma formation by manipulation of its microenvironment. *Plast Reconstr Surg.* 76:345-53). The up-regulation of certain channels and receptors during neuroma development can also cause abnormal sensitivity and spontaneous activity of injured axons (Curtin C and Carroll I. 2009. Cutaneous neuroma physiology and its relationship to chronic pain. *J. Hand Surg Am.* 34:1334-6). Haphazardly arranged nerve fibers are known to produce abnormal activity that stimulates central neurons (Wall P D and Gutnick M. 1974. Ongoing activity in peripheral nerves; physiology and pharmacology of impulses originating from neuroma. *Exp Neurol.* 43:580-593). This ongoing abnormal activity can be enhanced by mechanical stimulation, for example, from the constantly rebuilding scar at the injury site (Nordin M et al. 1984. Ectopic sensory discharges and paresthesiae in patients with disorders of peripheral nerves, dorsal roots and dorsal columns. *Pain.* 20:231-245; Scadding J W. 1981. Development of ongoing activity, mechanosensitivity, and adrenaline sensitivity in severed peripheral nerve axons. *Exp Neurol.* 73:345-364).

Neuromas of the nerve stump are unavoidable consequences of nerve injury when the nerve is not, or cannot be, repaired and can result in debilitating pain. It has been estimated that approximately 30% of neuromas become painful and problematic. This is particularly likely if the neuroma is present at or near the skin surface as physical stimulation induces signaling in the nerve resulting in a sensation of pain.

Neuroma prevention and attenuation strategies have used various methods to limit neuroma size and protect the neuroma from external stimuli. Current prevention methods attempt to limit the size of the neuroma and so reduce or limit potential contact and "cross-talk" between axons within the injured nerve site and within the disorganized structure that characterizes neuromas. Due to a variety of factors, current methods of neuroma mitigation/prevention have an unacceptable level of efficacy.

While various methods have been used to prevent, minimize, or shield neuromas, the current clinical "gold standard" for treating neuromas is to bury the nerve end (that will form the neuroma) into muscle or a hole drilled in bone. The surrounding tissue cushions and isolates the neuroma to inhibit stimulation and the resulting painful sensations. However this procedure can greatly complicate surgery, as significant additional dissection of otherwise healthy tissue is required to emplace the nerve stump. For these reasons, emplacement of the nerve stump is often not performed in amputations (and many other nerve procedures).

Another method is to cut the nerve stump back to leave a segment or sleeve of overhanging epineurium. This overhang can be ligated to cover the face of the nerve stump. Alternatively, a segment of epineurium can be acquired from other nerve tissue or a corresponding nerve stump can be cut back to create an epineurium sleeve that can be used to connect with and cover the other nerve stump.

Yet another method that is commonly used is a suture ligation, where a loop of suture is placed around the end of the nerve and tightened. This pressure is believed to mechanically block the exit of axons and causes the terminal end to eventually form scar tissue over the site. Clinical and pre-clinical evidence has shown, however, that this procedure can cause a painful neuroma to form behind the ligation. Furthermore, the ligated nerve is generally not positioned to minimize mechanical stimulation of the neuroma, since it is anticipated that the scar tissue will provide sufficient protection to the nerve end.

Other methods include covering the nerve stump with a silicone or rubber tube; a vein, or a silicone rubber plug (i.e. a tube with a sealed end) have also been used. These devices and methods necessitate insertion of the nerve into the opening of the device, which can be difficult and can further damage the nerve end. These methods and devices also maintain the neuroma as a single mass, whereby stimulation in one area creates a cascade effect that can eventually encompass the entire neuroma mass. Thus, even minor stimulation of a neuroma can cause the entire neuroma mass to react.

Unfortunately, current methods for addressing the formation of and pain caused by neuromas have not been generally successful and therefore are rarely utilized. The formation of neuromas at a severed nerve end can be difficult to prevent. As such, methods and devices that can inhibit or alleviate the pain caused by neuromas can provide relief to patients.

BRIEF SUMMARY

The subject invention provides devices and methods for alleviating discomfort associated with neuroma formation. Specifically, the subject invention provides biomedical devices and methods for neuroma size limitation and neuroma protection and isolation.

In preferred embodiments, the subject device is a cylindrical cap with a single open end to be applied to nerves within a subject's body, wherein the internal chamber of the cylindrical cap has separators or dividers that can physically partition the nerve structures into distinct, and in some embodiments, separate channels to enable a more regular arrangement, rather than the haphazard arrangement often produced in neuromas. Preferably the device is sterile and has a single open end, such that the nerve end can be inserted into the internal chamber through the open end. There can be a hollow indentation or retaining cavity between the open end and the separators or dividers in which the terminal end of the nerve can be situated and secured. As the nerve grows, the axons and other structures will extend and grown into the separate channels to limit contact between them.

In one embodiment, the partitioning of the internal chamber of the cap is in the form of a spiral-shaped wall that forms a longitudinal spiraled channel with one edge facing the open end. As nerve tissue grows, it can fill in the space between the spirals, so that the outer nerve tissue is substantially separated, subdivided, or partially subdivided from inner nerve tissue. In an alternative embodiment, the internal chamber is partitioned with at least one panel, directed longitudinally with the internal chamber, such that a portion of the internal chamber, opposite to the single open end, is divided into two or more distinct and separate channels. The division of the neuroma tissue into separate or subdivided channels, to form smaller, disconnected, neuroma masses, can mitigate the cascade effect caused when one area of the neuroma is stimulated and the effect is felt through the entire tissue mass. The dimensions of the cylindrical cap can be about 1 mm to about 25 mm in diameter and about 1 mm to about 100 mm in length.

In addition, the material of the cylindrical cap can remodel into a tissue cushion after implantation, thereby enveloping and further isolating the new neuronal growth, which protects the neuroma from being stimulated and inhibits pain. Remodeling can include, but is not limited to, expansion or enlargement of the material, reshaping of the material, incorporation of the material around nerve tissue, and other changes that can affect the size and shape of the material. Preferably, after the device is implanted, it will remodel into the surrounding tissue to protect the forming neuroma and the sections of smaller, disconnected neuromas mass. In one embodiment, the material of the cap is a biomaterial that can remodel to generate a volume of protective connective tissue around a neuroma (rather than the current use of a biomaterial to contain a neuroma volumetrically). In a preferred embodiment, the material of the cap is a membrane biomaterial, such as, for example, small intestine submucosa (SIS), amnion, dermis, or decellularized fascia.

In one embodiment of a method of use, a device is provided that contains an internal chamber with a retaining cavity at or near the open end to allow insertion of the nerve stump through the open end, so that it is near or abuts against the divided, or separate, channels facing the open end. A dense layer of biomaterial on the exterior surface can operate to mechanically isolate the neuroma and prevent axons from escaping the internal chamber of the device. The internal chamber contain partitions or dividers of biomaterial to subdivide the neuroma mass 13 into smaller, disconnected neuroma masses 17 as it grows that will form from the nerve stump.

Insertion of a terminal nerve end into the internal channel can be difficult. A terminal nerve end is one that has been cut or transected leaving exposed axons and other internal nerve structures. Usually, either the outside of the cap and/or the epineurium around the nerve are held with a forceps so the nerve can be moved through the open end. Excessive pressure applied to the nerve can damage internal axons and structures. Likewise, excess force applied around the cap can distort the shape or the open end, inhibiting insertion of the nerve end. An open end in the cap that is too large can allow the neuroma to escape and grow outside the cap. If the open end is made smaller, the nerve can be damaged if forced into the open end.

In one embodiment, to facilitate insertion of a terminal nerve end, a cap can have one or more tabs arranged on and around the external surface 16 of the cap. In an alternative embodiment, a tab can be arranged at or near the open end. The tabs can be used to grasp the cap and manipulate it around the terminal nerve end. Grasping the tabs rather than the exterior surface can help to maintain the shape of the cap, in particular the open end.

The open end leading into a retaining cavity in which the terminal nerve end can be secured can also be made temporarily larger or more accessible, so that the terminal nerve end can be more easily and gently placed therein. In one embodiment, there is a slit in the cap that is integral with and perpendicular to the opening, such that the opening can be temporarily widened. In another embodiment, the retaining cavity has one or more wings or flaps that allow it to be partially spread open. This can widen the open end sufficiently that a terminal nerve end can be placed or set down within the retaining cavity, making it easier to see how it is placed relative to the dividers. The wings or flaps can then be wrapped over and around the nerve end and secured to hold the nerve in place and inhibit escape of neuronal tissue growth.

The combination of limiting the growth and size of a neuroma mass through physical partitioning of the neuromas mass into smaller, disconnected sections along with the creation of a connective tissue cushion is unique. This novel combination of features and design effectively uses the natural response of reconstructing implanted biomaterials to minimize the size, isolate, and protect the neuroma.

BRIEF DESCRIPTION OF THE DRAWINGS

FIGS. 1A, 1B and 1C show a schematic presentation of consecutive steps of various current nerve stump capping methods: Step 1—nerve transection; Step 2—nerve stump preparation (A and B, nerve sheath must be slid off, then a piece of the nerve is removed to prepare a sleeve-like fragment of epineurium; C, cap can be formed of any autologous tissue, sutured to the epineurium); Step 3—the end of epineurium can be tied up or sutured. Lewin-Kowalik J. et al. (2006) Prevention and Management of Painful Neuroma. *Neurol Med Chir* (Tokyo), 46:62-68.

FIGS. 2A, 2B and 2C show perspective views (2A and 2C) of two embodiments of the invention and a side view (2B) of an embodiment of the device of the subject invention.

FIGS. 3A and 3B show a side cut-away view (FIG. 3A) of and top view of the proximal end (FIG. 3B) of the embodiment.

FIG. 4A is a schematic drawing showing an untreated neuroma.

FIG. 4B is a schematic drawing showing a neuroma treated using an embodiment of a device of the subject invention.

FIG. 6A is a proximal end perspective view of an embodiment. FIG. 6B is top side, proximal end perspective view of the embodiment. FIG. 6C is a right side elevation view of the embodiment. FIG. 6D is a top side plan view of the embodiment. FIG. 6E is a left side perspective view of an alternative embodiment of a cap with a tab extending from the edge of the open end.

FIGS. 7C and 7D illustrate an alternative embodiment where more than one panel is arranged parallel with each other in the internal cavity.

FIG. 8A shows an embodiment with one flap and FIG. 8B shows an embodiment with two flaps. FIG. 8C illustrates how distal edge of the flaps can open directly onto the separate channels. FIG. 8D illustrates an alternative embodiment where the distal edges of the flaps open proximal to the separate channels. FIG. 8E shows a non-limiting example of a cap with a slit at the open end, such that there is are tri-corner flaps that can be used to temporarily widen the open end.

DETAILED DISCLOSURE

Figure 5A:
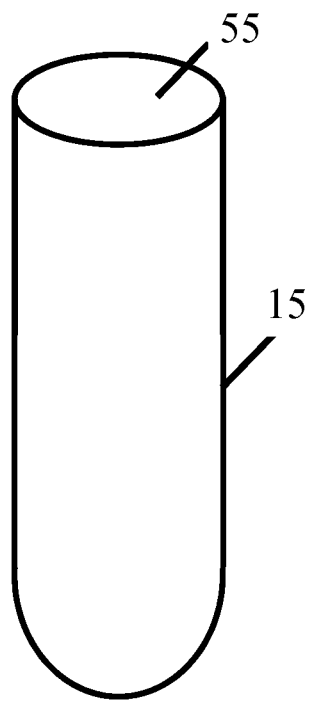
FIG. 5A is a schematic drawing showing a perspective view of another embodiment of the device of the invention.

The subject invention provides devices and methods for alleviating discomfort associated with neuromas. More specifically, the subject invention pertains to devices and methods for limiting neuroma size and physically surrounding the neuroma to inhibit stimulation that elicits neuropathic pain. In certain embodiments, the subject invention is directed to a tissue-engineered scaffold that provides: a barrier that limits the size of a neuroma, dividers that subdivide the neuroma volume or mass into smaller, disconnected neuromas masses to reduce axonal cross-talk or the "cascade effect," and mechanical isolation of the neuroma to inhibit stimulation.

A device of the subject invention is designed to form a protective, connective tissue covering or cap surrounding the terminal nerve end 29, thereby surrounding any resulting neuroma formation. Within the volume created by the barrier, sub-dividing the neuroma volume as it forms can limit the amount of interaction between axons, thereby limiting signaling cascades being triggered inside the neuroma that can be interpreted as pain. By providing mechanical isolation of the neuroma volume, the subject device limits stimulation of the neuroma. The ability of the material of the subject device to remodel into a native tissue cushion is another advantageous feature when combined with the physical partitioning of the neuroma.

Current methods for limiting the size and stimulation of a neuroma are shown in FIGS. 1A-1C. The methods include dissecting or cutting the terminal end to form a flap of epineurium that can be folded over the terminal nerve end 29, as shown in the first column of FIGS. 1A-1C. The nerve can also be dissected or cut back to form a sleeve of epineurium that can be ligated over the terminal nerve end, as seen in the middle column in FIGS. 1A-1C. A patch epineurium can be obtained from another location and attached to the terminal nerve end, as shown in the last column in FIGS. 1A-1C.

The subject invention provides the benefits of an epineural flap (or ligation) to limit neuroma size and the advantages of isolating a nerve end by emplacement in another tissue combined in a single device. This device isolates and protects the neuroma, thereby inhibiting painful sensations without the need for any repositioning of the nerve. Advantageously, the device can be secured to the stump of the nerve prior to formation of a neuroma and as the neuroma forms the material of the device can remodel into a tissue cushion 55 and become integrated into the surrounding host tissues, which effectively isolates the neuroma from undesirable contact and stimulation.

FIGS. 2A-8B illustrate embodiments of the invention. In one embodiment, illustrated in FIG. 2, the cap 10 of the subject invention has an external body 15 that comprises a proximal end 20 and a distal end 25.

It can be seen in FIG. 2 that one embodiment of the external body 15 of the cap 10 is cylindrical in shape. However, the shape of the external body 15 of the cap 10 can vary depending upon the type, diameter and location of a nerve stump, as well as other factors known to those with skill in the art. For example, the circumferential shape of the external body can be variable and be, by way of non-limiting examples, an ovoid, a circle, a square, a rectangle, a triangle, or any other polygonal shape. In an exemplified embodiment, the circumferential shape of the external body is generally a circle.

The dimensions of the external body can vary depending on the type, diameter and location of a nerve stump on which it will be used, as well as other factors known to those skilled in the art. In one embodiment, the external body of the device has dimensions of approximately 1 mm to approximately 100 mm in diameter and is approximately 1 mm to approximately 500 mm in length, between the proximal end 20 and the distal end 25. In a particular embodiment, the external body of the device will be less than 100 mm in diameter and less than 500 mm in length. In a specific embodiment, the diameter of the external body is between approximately 1 mm and approximately 25 mm and the length of the external body, between the proximal end and the distal end of the cap, is between approximately 1 mm and approximately 100 mm.

In one embodiment, the diameter of the distal end 25 of the external body 15 can be narrower than the diameter of the proximal end 20, as seen, for example, in FIGS. 2 and 3. This can give the cap a bullet or conical shape. In a particular embodiment, shown for example in FIGS. 2A-2C, the distal end 25 of the external body is cone-shaped. In an alternative embodiment, shown for example in FIGS. 6A-6E and FIGS. 7A-7B, the diameter of the distal end and the proximal end are the same or substantially the same, such that the distal end of the cap is fat, giving the cap a cylinder or barrel shape.

Ideally, the external body 15 of the cap 10 has no openings other than the open end 18 at the proximal end 20 of the cap through which a nerve can be inserted or placed. In one embodiment, for example, as shown in FIG. 3, the proximal end 20 is open and the distal end 25 of the external body 15 is closed off entirely so that the external body forms a cap 10. FIG. 3 also illustrates an embodiment in which an internal chamber 35 is provided in the external body 15. In certain embodiments, the interior surface 22 of the closed off 30 portion of external body 15 can be in the form of a bevel 40, as shown in FIG. 3A. Alternatively, a closed off portion can be substantially flat, as shown in FIGS. 6C and 7A. In yet another alternative, the closed off portion or closed end 30 can be conical, such as shown, for example, in FIGS. 2A and 6E.

An external body without excess openings can inhibit axon growth from extending outside the cap. The open end 18 of the cap can provide the only access into the internal chamber. Fitting a terminal nerve end 29 through the open end of a cap can be challenging and can potentially damage the nerve. If a cap with a larger diameter is selected, it can be easier to insert the terminal nerve end, but may result is excess space around the nerve perimeter. If not properly closed off, the openings around the nerve can allow axons to escape.

Figure 8A:
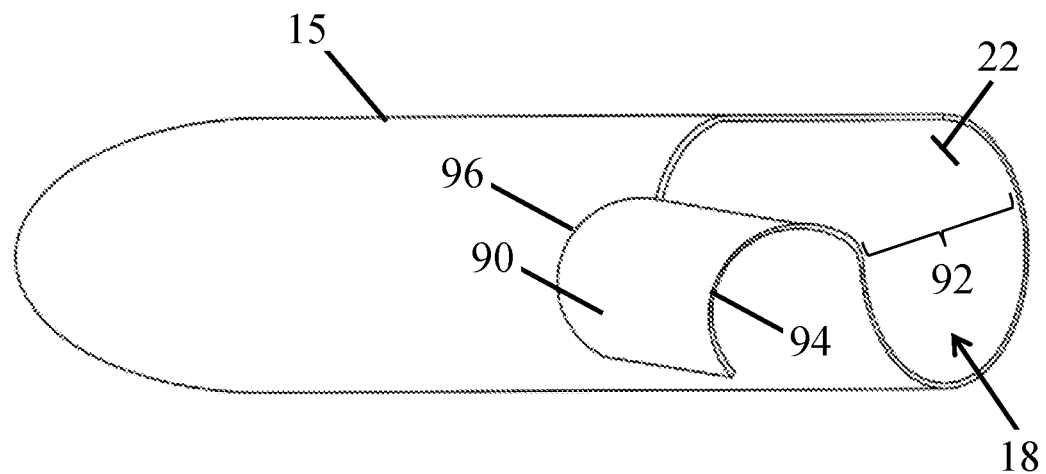
FIGS. 8A, 8B, 8C, 8D, and 8E illustrate embodiments of a cap, according to the subject invention, where the open end is configured with one or more flaps that partially spread or widen the open end to allow a terminal nerve end to be more easily placed within the retaining cavity.

The use of flaps 90 around the open end 18 can provide a temporary enlargement of the open end, making nerve placement into the internal chamber easier, while the flap can be wrapped around and sutured to provide for a close fit around the terminal nerve end. The enlargement of the open end allows a terminal nerve end to be moved through a slot 92 formed in the open end. FIGS. 8A and 8E illustrate non-limiting examples of a cap having an open end 18 with one or more flaps. Ideally, the slot provided by one or more flaps is large enough to allow a terminal nerve end to pass through the slot, with minimal compression of the nerve tissue, so as to minimize the number of sutures necessary to close the flap and the slot.

In one embodiment, there is a single flap, as shown in FIG. 8A. The single flap can provide a slot of between approximately 25% to approximately 75% of the diameter of an opening 18. In a more particular embodiment, there is a single flap that provides a slot of between approximately 35% to approximately 65% of the diameter of the opening. In a specific embodiment, there is a single flap that provides a slot of between approximately 45% to approximately 55% of the diameter of the opening. In a specific embodiment, there is a single flap that provides a slot of approximately 50% of the diameter of the opening.

Figure 8B:
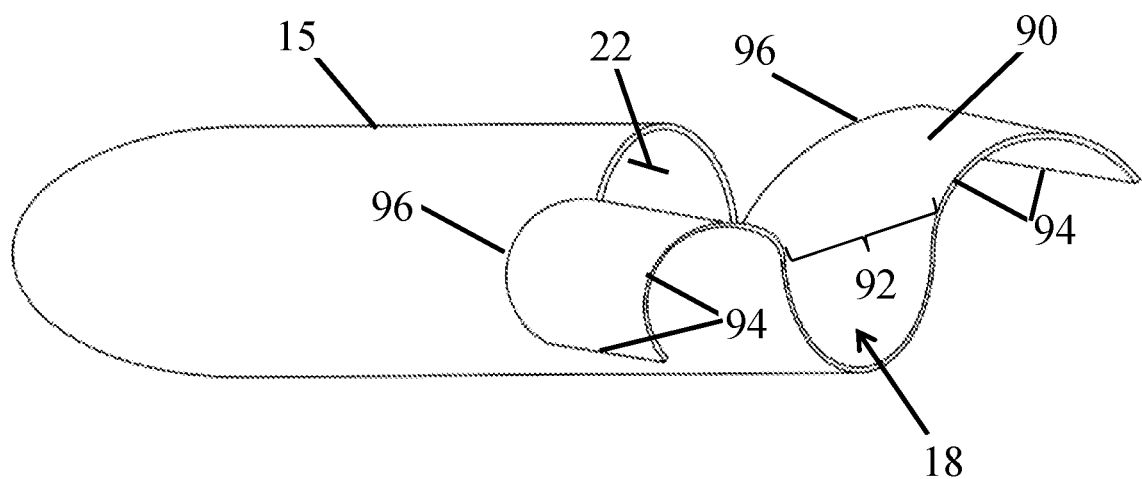
Figure 8C:
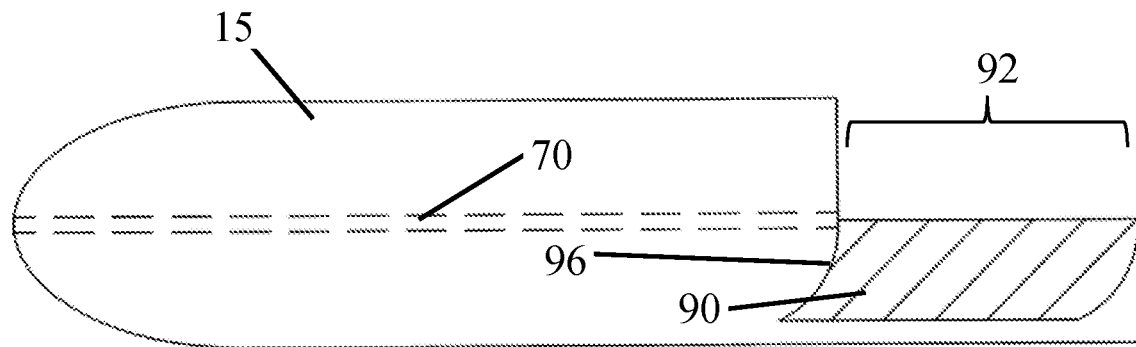
Figure 8D:
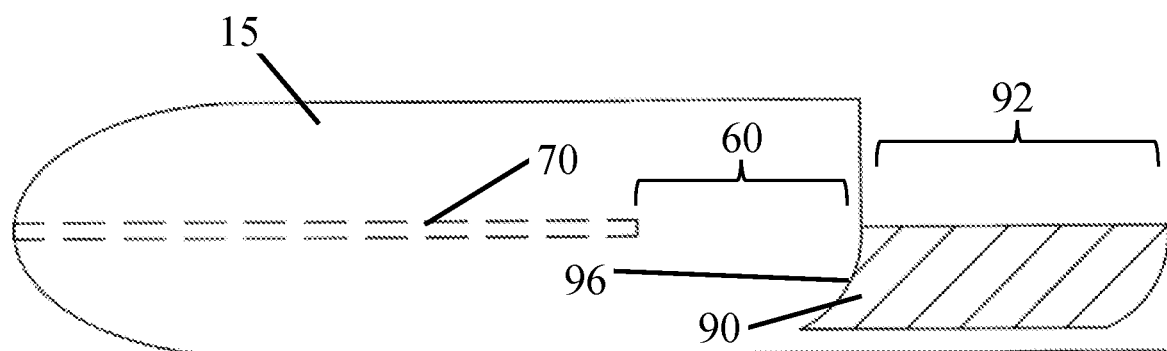
Figure 8E:
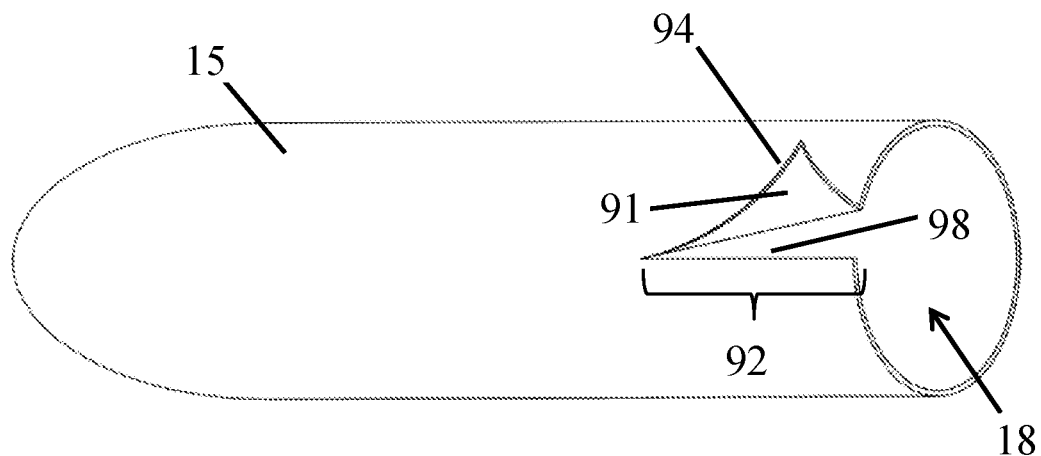

In an alternative embodiment, there are two flaps, as shown in FIG. 8B. The dual flaps can open in opposite directions. The dual flaps can provide a slot of between approximately 25% to approximately 75% of the diameter of an opening 18. In a more particular embodiment, there is a single flap that provides a slot of between approximately 35% to approximately 65% of the diameter of the opening. In a specific embodiment, there is a single flap that provides a slot of between approximately 45% to approximately 55% of the diameter of the opening. In a specific embodiment, there is a single flap that provides a slot of approximately 50% of the diameter of the opening.

In an alternative embodiment, there is a slit 98 in the proximal end 20 of the cap that is integral with opening 18 and that advances towards the distal end 25 to form a flap with three corners part-way along the external body 15 of the cap. FIG. 8E illustrates a non-limiting example of a three-corner flap.

The nerve tissue in a neuroma mass 13 grows in a random, haphazard fashion and the axons in one section of a neuroma can be in contact with other surrounding axons. This creates the disadvantageous effect of the neuroma acting as one, open nerve end. As a result, stimulation of a neuroma in one area can trigger a cascade effect wherein the signal received by axons in one area, because of contact, will trigger signals in nearby axons. Each step in the cascade can amplify the initial signal until finally most or all of the axons in the neuroma are "fired." This massive signal cascade can also amplify pain. By isolating or separating areas of the neuroma from other areas of the neuroma, this cascade effect can be minimized, thereby limiting the amount of pain caused by stimulation of the neuroma.

In one embodiment, the internal chamber 35 can be configured with one or more dividers 70 that subdivide at least a portion of the internal chamber into two or more separate channels 36 into which the neuroma mass 13 can grow and become portioned into smaller, disconnected neuroma masses. This separation of the neuroma mass into the different channels creates a physical barrier between the axons of the smaller, disconnected portions in the different separate channels, thereby limiting the scope of a cascade effect. The dividers 70 used in an internal chamber can be configured in a myriad of ways to create different sizes and shapes of separate chambers. Likewise, the dividers can be individual or unconnected or they can be joined together. Variations in the configurations of the dividers that separate a neuroma mass into smaller, disconnected masses 17 or portions with different channels are within the scope of this invention.

A nerve end can be positioned within the cap 10 so that the neuronal growth is directed towards the closed end 30 and the separate chambers. It can be beneficial if there is some overlap between the external body and the epineurium, so as to provide space or distance between the end of the nerve and the open end when the terminal nerve end 29 is secured in the cap. This can be achieved by having the dividers 70 terminate some distance from the open end, thereby forming a retaining cavity 60 between the open end 18 and a divider. FIGS. 6A, 6C, 7A, and 7D illustrate non-limiting examples of dividers that are shorter than the length, between the distal end and the proximal end of the cap, of the external body 15. The termination of the dividers before the open end forms an undivided retaining cavity in which the terminal nerve end can be disposed. The subsequently forming neuroma will be directed towards the separate channels and divided into separate, smaller, disconnected portions or volumes as it grows into the separate channels.

In one embodiment, a divider is shorter than length of the internal chamber, such that between approximately 25% to approximately 75% of the internal chamber is divided into separate channels. In a more particular embodiment, a divider is shorter than the length of the internal chamber, such that between approximately 40% and 60% of the internal chamber is divided into separate channels. In a specific embodiment, a divider is shorter than the length of the internal chamber, such that approximately 50% of the internal chamber is subdivided into separate chambers.

According to one embodiment of the invention, the external body 15 can have an internal chamber 35 that includes spiral partitions 45. Advantageously, the spiral partitions enable subdivision and arrangement of axons from the nerve stump. In certain related embodiments, the internal chamber of the external body comprises a tightly packed spiral of a solid sheet of biomaterial. Preferably, where the internal chamber of the external body comprises a tightly packed spiral of a solid sheet of biomaterial, there are no voids present that could lead to axonal escape from the device.

In an alternative embodiment, the internal chamber can be subdivided by separate concentric tubes 46, such as shown, for example, in FIG. 2C. The concentric tubes 46 can also partition or subdivide the internal chamber, enabling the formation of smaller, disconnected neuromas masses 17. In another embodiment, the divider 70 is a panel that extends across and attaches to the internal surface 22 of the internal chamber 35. The panel divider can extend from the closed portion 30 at distal end 25 and towards the open end 18 proximal end 20 thereby dividing the closed off portion 30 of the internal chamber in a longitudinal direction 28 into two separate channels 36. In a further embodiment, the panel divider extends partially through the internal chamber, such that a portion of the internal chamber is subdivided and another portion, nearer the proximal end, remains undivided. FIGS. 6A-6D illustrate a non-limiting example of this embodiment. In a further embodiment, there can be more than one panels so that the internal chamber is divided into more than two separate channels. FIGS. 7A and 7B illustrate non-limiting examples of 2 and 3 panels arranged perpendicularly, dividing the internal chamber into four quadrants. FIGS. 7C and 7D illustrate another non-limiting example of multiple panels arranged parallel within the internal chamber, dividing the internal chamber into similar parallel, separate channels. Other arrangements of panels that form different configurations of separate channels are within the scope of this invention.

In one embodiment, a panel extends in a longitudinal direction 28 between approximately ¼ to approximately ¾ of the length, between the proximal end 20 and the distal end 25 of the internal chamber. In a more specific embodiment, a panel extends in a longitudinal direction between approximately ⅖ to approximately ⅗ of the length of the internal chamber. In a specific embodiment, a panel extends approximately ½ of the length of the internal chamber.

The flaps 90, mentioned above, can provide a slot 92 that allows the terminal nerve end 29 to be placed in close proximity to the dividers 70. In one embodiment, the flaps have a rear edge 96 that allows the flap to open onto the dividers, so that the slot is directly open to the dividers, allowing a terminal nerve end to be placed against the dividers, which is shown, for example, in FIG. 8C. In another embodiment, the flaps have a rear edge 96 that is proximal to the dividers, such that the flap opens more proximal 20 to the dividers, providing for at least a small retaining cavity 60 between the rear edge or the slot and the dividers, such as shown, for example, in FIG. 8D.

In an alternative embodiment, the flap is formed by a slit 98 in the external body of the cap, extending from the opening towards the distal end. FIG. 8E illustrates a non-limiting example of a flap formed by a single slit 98 in the external body. The slit can extend part-way towards the distal end, such that it terminates at the dividers 70, such that the slot 92 opens onto the dividers. Alternatively, the slit 98 can terminate proximal to the dividers, such that the slot 92 opens more proximal or a distance in front of to the dividers, providing for at least small retaining cavity 60 between the dividers and the end of the distal end of the slit.

In one embodiment, as illustrated in FIG. 4B, the internal chamber 35 is an unchambered or undivided layer of biomaterial 50. The biomaterial preferably isolates the neuroma and prevents axons from escaping the external body 15 of the device. FIG. 4A is a schematic drawing showing an untreated neuroma.

Both natural and synthetic biomaterials can be used to manufacture a cap and components thereof of the subject invention. In certain embodiments, the biomaterial is a homogenous material. Examples of biomaterials for use in manufacturing the subject invention include, but are not limited to, high density polyethylene (HDPE), polyethylene glycol (PEG) hydrogel, purified proteins from human or animal sources (e.g., membrane of purified collagen or fibrin), and decellularized tissue constructs (e.g., demineralized bone, amnion. SIS, dermis, or fascia). An HDPE or PEG device can comprise or consist of a cylinder of porous HDPE or PEG surrounded by a layer of non-porous HDPE or PEG. Biomaterials that can form a fluid material, such as soluble purified collagen or particulate SIS and dermis, can be directly cast to form the device without a membrane as an intermediate.

In certain embodiments, the external body 15 of the device can be made by rolling a sheet of biomaterial to form spiral partitions. Where the external body of the device is a "roll" of spiral partitions, the layers of the roll separate slightly to allow nerve regeneration to proceed a short distance into the device before encountering, and being stopped by, infiltrating non-nerve tissue (i.e., the rolled version has longitudinal pores or characteristics). In specific related embodiments, layers of the rolled biomaterial are situated such that a spiral channel is present on the face of the device facing the nerve stump, while the device face external to the nerve stump is solid.

In other embodiments, the external body of the device can be made of a porous biomaterial. In yet other embodiments, the body includes a hollow central cavity to facilitate insertion of a nerve stump. In certain other embodiments, a body is provided with a hollow cavity wherein layers of biomaterial scaffolding fill a portion of the hollow cavity to create a laminar or multi-laminar construct 60 (see FIG. 2C).

In an alternate embodiment, as illustrated in FIG. 5A, the external body 15 of the device resembles a test tube, where the body is made of a thin layer of biomaterial (either a single layer or multiple layers) and there is a hollow central cavity 55 to facilitate insertion of a nerve stump.

Figure 5B:
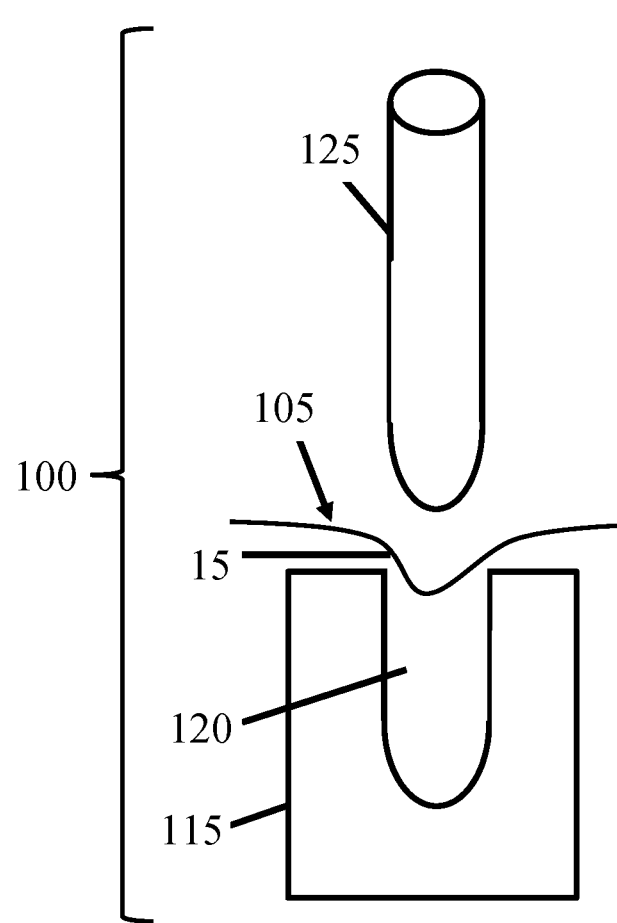
FIG. 5B is a view illustrating a press-forming process executed by the press-forming apparatus to manufacture an embodiment of the device shown in FIG. 5A.

Illustrated in FIG. 5B is a method for producing the embodiment of the device shown in FIG. 5A. FIG. 5B illustrates a press formation apparatus 100 for manufacturing the device of FIG. 5A. As shown in FIG. 5A, a thin layer of biomaterial 105 (formed from either a single layer or multiple layers of biomaterial) is mounted on a receiving portion 115 of the press formation apparatus 100. The receiving portion 115 has an opening 120 for receiving a punch 125, where the shape of the opening 120 corresponds with that of the punch 125. The receiving portion 115 and the punch 125 can be manufactured by die molding. Preferably, the punch 125 is rod shaped; however, other shapes known to the skilled artisan can be used for the opening of the receiving portion and the punch.

The thin layer of biomaterial 105 is arranged over the opening 120 of the receiving portion 115. Once the biomaterial 105 is positioned, the punch 125 is then driven downward and received in the opening 120. In this way, the body 15 of the device is formed.

In further embodiments, a cylindrical body having a hollow interior with open ends is provided. The distal end of the body may be "crimped" during the manufacturing process to present a more solid biomaterial as a barrier to axonal escape from the device. An example is the use of a crimped mold during vacuum pressing of a rolled cylinder, such that one end is of a smaller diameter.

In a preferred embodiment, the body of the subject device comprises a cylinder of SIS. A hollow cavity is provided at the proximal end to allow insertion of a nerve stump. A deep spiral partition is present in the body to subdivide the neuroma that will form from the nerve stump, and a dense layer of biomaterial is provided on the entire exterior surface to mechanically isolate the neuroma and prevents axons from escaping the device.

In a method of use, a nerve stump is secured in the internal chamber 35 by means of a suture, staple, clip, or surgical adhesive or sealant. After implantation, the cap is remodeled into the body's own tissue and provides a tissue cushion 55 for the neuroma. As host cells infiltrate the biomaterial, it is converted into a form of connective tissue. Axons and Schwann cells will also infiltrate from the stump. As fibroblasts (and other cells supporting remodeling into a connective tissue) 1) migrate and proliferate faster than Schwann cells/axons and 2) infiltrate from multiple sides and 3) axonal regeneration stops when it encounters other tissues (such as muscle, connective tissue layers, etc); the device will result in a layer of connective tissue surrounding a small neuroma in a vascularized tissue capsule. This capsule provides the desired isolation and protection.

It can be beneficial for the nerve end to be fully encapsulated within the cap, so that when the nerve begins to grow and form a neuroma, all neuronal growth is contained within the cap and, preferably, directed towards the separate channels at the closed end 30. Manipulation of a terminal nerve end 29 into a cap can be difficult. Nerve tissue is usually soft and susceptible to damage if too much force is applied. Typically, the cap is manipulated onto the terminal nerve end. The cap can be grasped or encircled by various instruments to manipulate it onto the terminal nerve end. This can distort the shape of the external body and make it difficult to manipulate onto the terminal nerve end.

In one embodiment, the external body 15 is configured with one or more tabs 80 extending out from the external body. The tabs can provide points for grasping the cap without contacting, or by making minimal contact, with the external body. A tab can be any size or shape and there can be more than one tab on an external body. Preferably, the size and shape of a tab provides opposing surfaces 82 for grasping with a forceps or any other instrument with pincers that can be squeezed together to grasp or hold small structures. A tab can also be used as a connection point, wherein by the cap and a terminal nerve secured therein can be attached to another structure in the body using a tab. In one embodiment, a tab comprises the same or similar material as the cap. For example, a tab can be formed from the same biomaterial that the cap is formed from, allowing the tab to be remodeled with the cap, as described above. In an alternative embodiment, the tab comprises a different material than the cap. For example, a tab can comprise a polymer that dissolves or is absorbed by the body. After the tab has been used to manipulate the cap into position, the tab can be left in place on the cap. Alternatively, a tab can be removed from the cap, such as by cutting with a scissors, blade, or compression sealing.

Figure 6A:
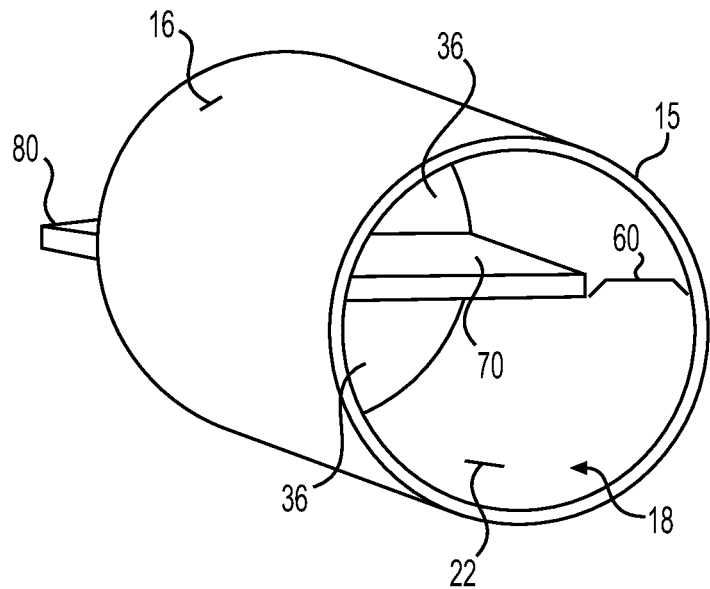
FIGS. 6A, 6B, 6C, 6D, and 6E illustrate embodiments of a cap, according to the subject invention, configured with a tab by which the cap can be manipulated and an internal panel that subdivides a portion of the distal end of the internal chamber into separate channels.
Figure 6B:
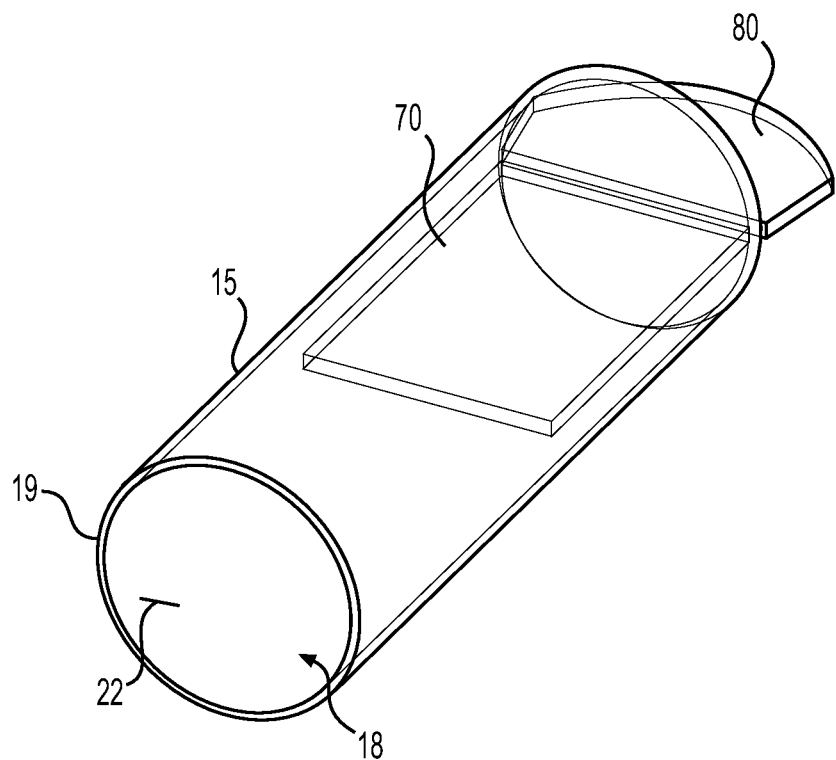
Figure 6C:
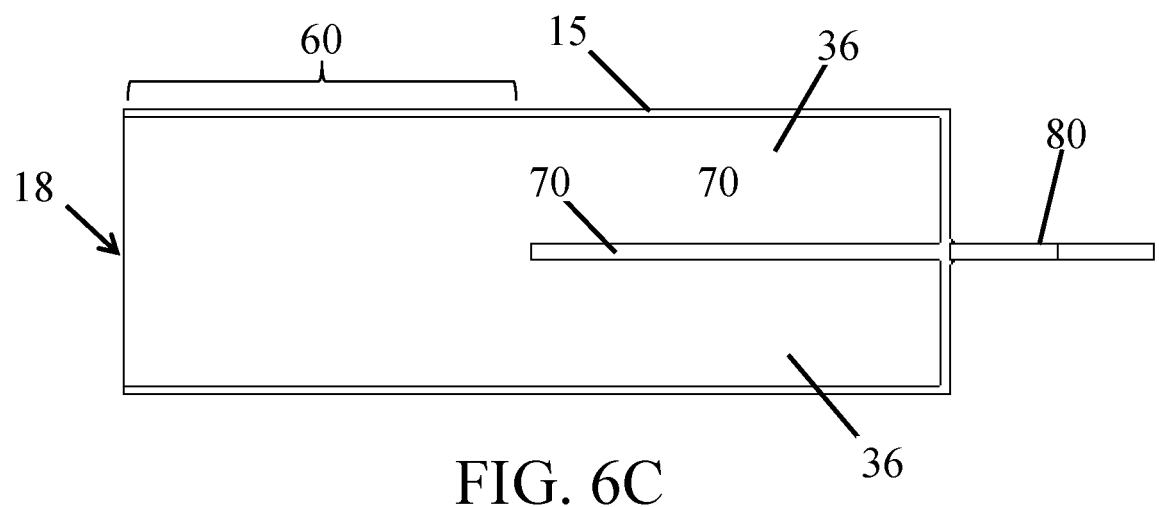
Figure 6D:
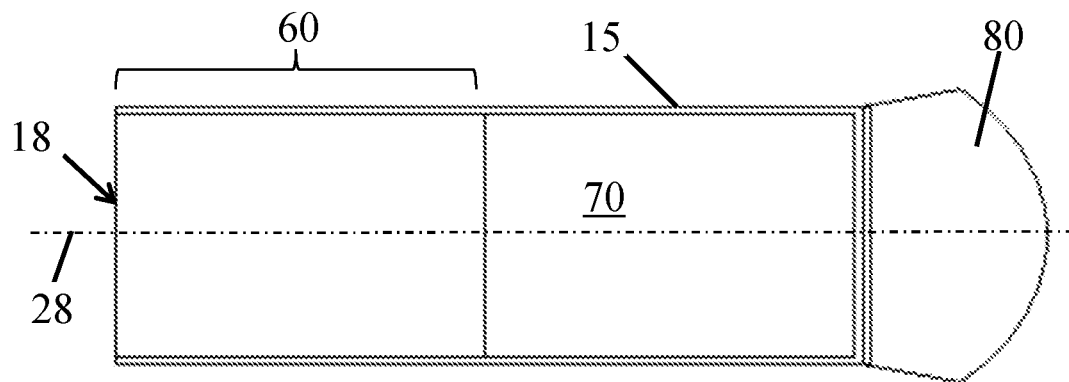
Figure 7A:
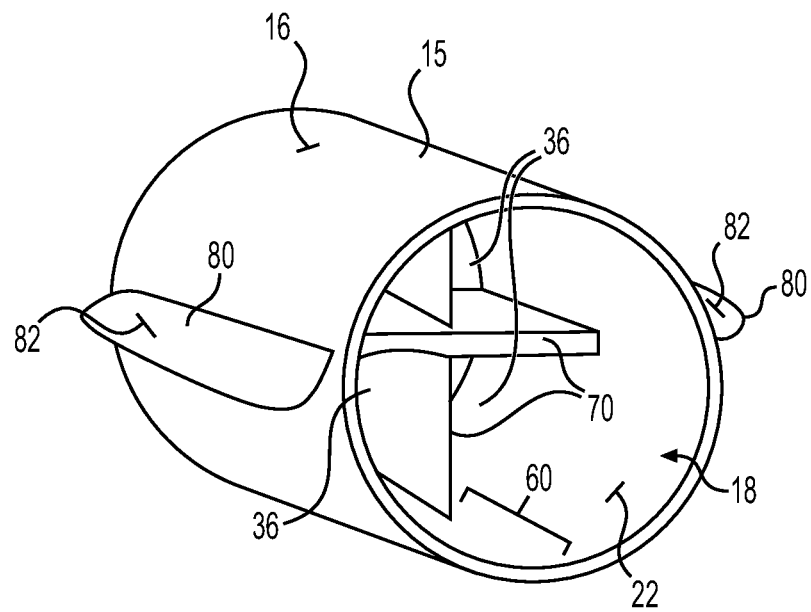
FIGS. 7A, 7B, 7C and 7D illustrate an embodiment of a cap, according to the subject invention, configured with multiple tabs by which the cap can be manipulated and also shows several internal panels that subdivide a portion of the distal end of the internal chamber into multiple separate channels. The example shown in FIGS. 7A and 7B has a tab at the distal end and two tabs on the right and left sides. Also shown in this example are three perpendicularly placed panels within the internal chamber.
Figure 7B:
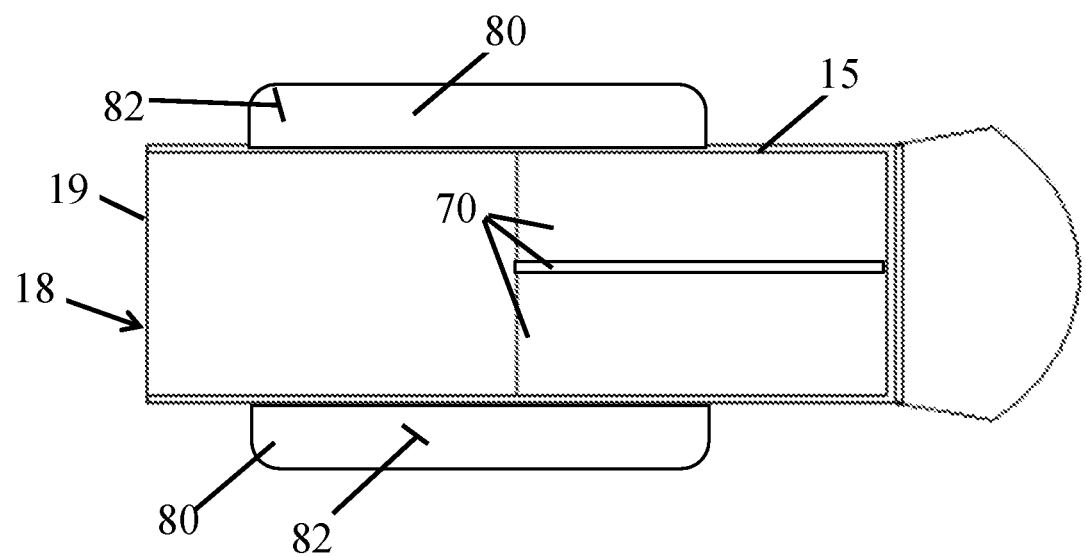
Figure 7C:
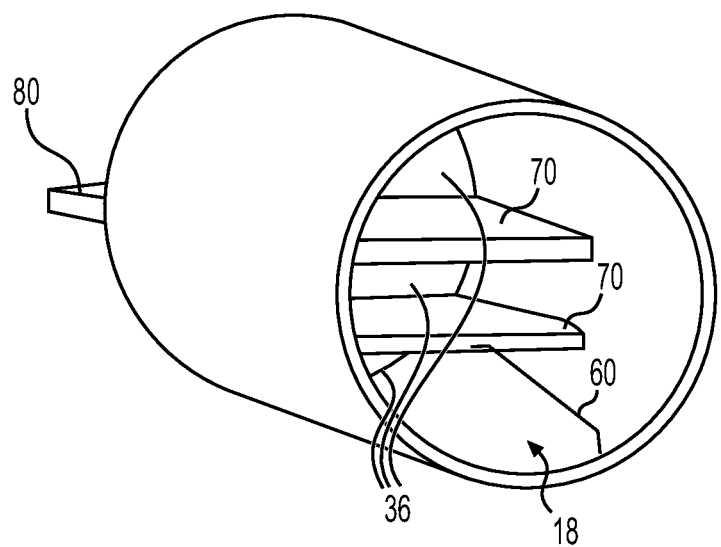
Figure 7D:
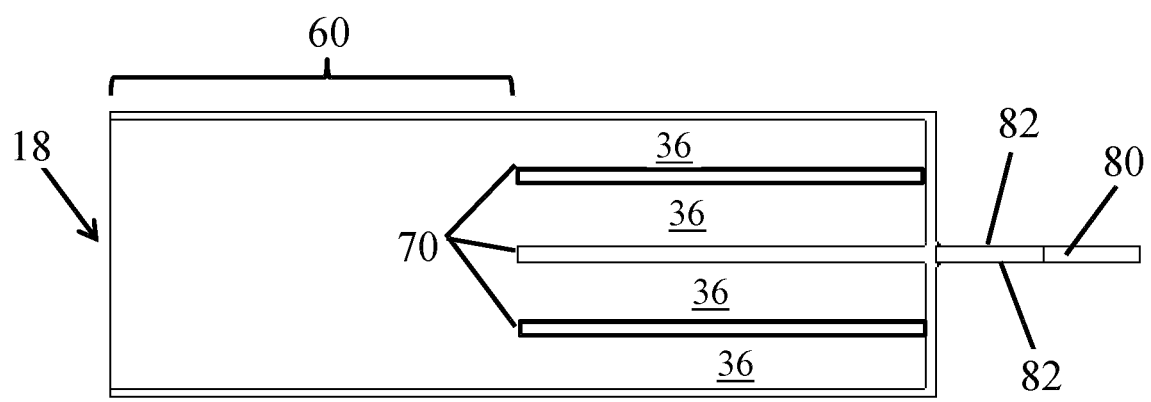

In one embodiment, a tab extends out from the closed end 30 of the cap 10, such as shown, for example, in FIGS. 6B, 6C, and 6D. In these Figures, the tab is shown traversing the full diameter of the closed end. This is not required and the width of the tab can be less than the diameter of the cap, which is not shown, but is understood by a person with skill in the art.

Figure 6E:
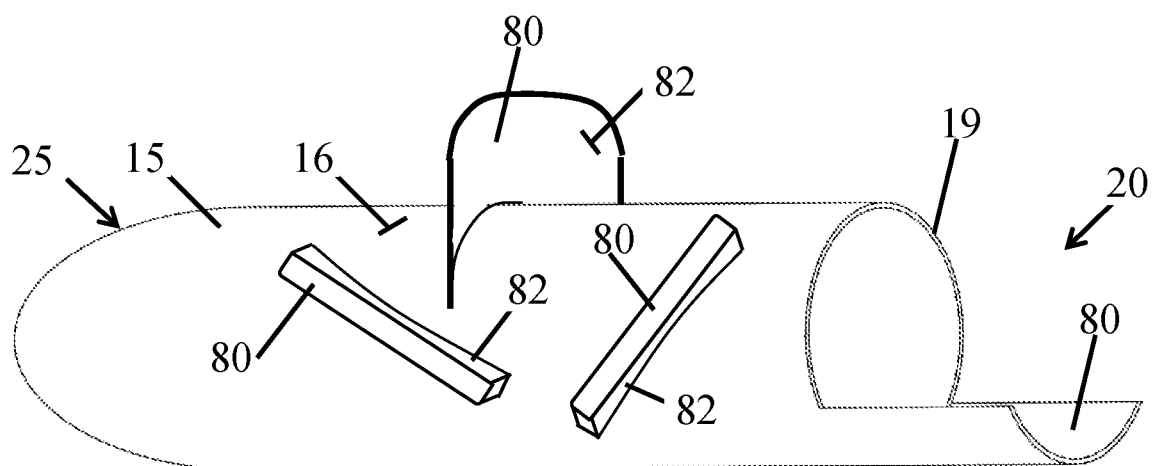

In another embodiment, a tab can extend from the open end 18 of the cap 10, such that it forms a lip or shelf around the edge 19 of the open end. FIG. 6E illustrates one example of a tab 80 extending from the edge 19 of the open end 18. This type of tab can be used to pull the cap onto a terminal nerve end. A tab extending from the edge of the open end can also support a terminal nerve end placed thereon and other tabs on the external body 15 can be used to push the cap onto the terminal nerve end.

In addition to tabs that can be used to push or pull a cap onto a terminal nerve end 29, tabs can be located in and extend from other areas of the cap and used to twist, turn, rotate, or otherwise manipulate a cap 10 onto a terminal nerve end. In another embodiment, at least one tab extends out from or away from a side of the external body. One example of this is shown in FIGS. 7A and 7B, where two tabs are shown extending out from each side of the external body.

Furthermore, tabs can be arranged in any of a myriad of orientations on the external body. One embodiment, shown in FIG. 7B, has at least one tab arranged with an opposing surface parallel with, or approximately parallel with, the longitudinal direction 28 of the internal chamber 35. FIG. 6E shows an alternative embodiment where the tab is arranged with an opposing surface perpendicular, or approximately perpendicular, to the longitudinal direction of the internal chamber. Tabs can also be arranged with an opposing surface, relative to the opening 18, at an oblique angle with the longitudinal direction of the internal chamber. A person with skill in the art will be able to determine, for one or more tabs, the appropriate location on the external body and orientation with respect to the longitudinal direction of the internal chamber. Such variations are within the scope of this invention.

Neuroma formation occurs in approximately 30% of severed nerve ends. Without intervention, neuroma formation can form a randomly arranged conglomeration of axons. This haphazard arrangement of axons makes the neuroma susceptible to a cascade effect when the neuroma is stimulated, where stimulation in one area radiates and intensifies through the entire neuroma mass, resulting in intense pain. The embodiments of the subject invention can mitigate the effects of a cascade effect with caps that can be attached to terminal nerve ends. The caps can aid in reducing the size of a neuroma and can provide channels for mechanical separation of a neuroma mass, thereby limiting the effect of stimulation of the neuroma. The caps of the subject invention also have external tabs and flaps that can aid in fitting the cap over a terminal nerve end. The caps of the subject invention represent a significant improvement in amelioration of the pain caused by neuromas.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein are incorporated by reference in their entirety, including all figures and tables, to the extent they are not inconsistent with the explicit teachings of this specification.

We claim:

1. A device for alleviating discomfort associated with neuroma formation, the device comprising:
   a body having an open proximal end and a closed distal end;
   an internal chamber defined by the body;
   at least one divider within the internal chamber that subdivides at least a portion of the internal chamber, wherein the at least one divider extends from a distal end of the internal chamber to a region between the proximal end of the body and the distal end of the internal chamber so that the at least one divider subdivides 25% to 75% of a length of the internal chamber into separate channels;

wherein the internal chamber includes an undivided retaining cavity located between the proximal end of the body and a proximal end of the at least one divider; and at least one tab extending out from an external surface of the body.

2. The device of claim 1, wherein the body of the device is 1 mm to 500 mm in length.

3. The device of claim 1, wherein the body of the device is 1 mm to 100 mm in diameter.

4. The device of claim 1, wherein the at least one divider extends along 40% to 60% of the length of the internal chamber.

5. The device of claim 1, wherein the at least one divider extends along 50% of the length of the internal chamber.

6. The device of claim 1, wherein the at least one divider is a panel divider.

7. The device of claim 1, wherein the at least one divider includes a plurality of panel dividers so that the internal chamber is divided into more than two separate channels.

8. The device of claim 7, wherein the plurality of panel dividers includes at least two panel dividers arranged perpendicular to one another.

9. The device of claim 7, wherein the plurality of panel dividers includes at least two panel dividers arranged parallel to one another.

10. The device of claim 1, wherein the at least one tab includes a tab extending out from the distal end of the body.

11. The device of claim 10, wherein the tab extending out from the distal end of the body lies in a plane that includes the at least one divider.

12. The device of claim 1, wherein the at least one tab includes a tab extending out from a side of the body.

13. The device of claim 1, wherein the at least one tab incudes a tab extending parallel to a longitudinal axis of the device.

14. The device of claim 1, wherein the at least one tab incudes a tab extending perpendicular to a longitudinal axis of the device.

15. The device of claim 1, wherein the at least one tab incudes a tab extending at an oblique angle relative to a longitudinal axis of the device.

16. The device of claim 1, wherein the body has a diameter at a distal end region that is less than a diameter at a proximal end region.

17. The device of claim 1, wherein the body has a diameter at a distal end region that is equal to a diameter at a proximal end region.

18. The device of claim 1, wherein the device comprises a biomaterial selected from the group consisting of: high-density polyethylene (HDPE), polyethylene glycol (PEG) hydrogel, purified protein from human or animal sources, and decellularized tissue constructs.

19. The device of claim 18, wherein the biomaterial is selected from the group consisting of: collagen, fibrin, demineralized bone, amnion, small intestine submucosa (SIS), dermis, or fascia.

20. The device of claim 19, wherein the device comprises porous HDPE or PEG surrounded by a layer of non-porous HDPE or PEG.

21. The device of claim 1, wherein the body has a cylindrical shape.

22. The device of claim 1, further comprising a slit extending from the proximal end towards the distal end.

23. The device of claim 22, wherein the body includes one or more flaps that at least partially surround the retaining cavity.

24. The device of claim 1, further comprising at least one flap.

25. The device of claim 24, wherein the at least one flap includes a single flap that extends along at least one of: (i) 25% to 75% of a periphery of the open proximal end; (ii) 35% to 65% of a periphery of the open proximal end; or 45% to 55% of a periphery of the open proximal end.

26. The device of claim 24, wherein the at least one flap includes two flaps that together extend along 25% to 75% of a periphery of the open proximal end.

27. The device of claim 24, wherein the at least one flap includes two flaps that are configured to open in opposite directions from one another.

28. The device of claim 24, wherein at least a portion of the retaining cavity is located between a distal edge of the at least one flap and the proximal end of the at least one divider.

29. The device of claim 24, wherein none of the retaining cavity is located between a distal edge of the at least one flap and the proximal end of the at least one divider.

30. The device of claim 24, wherein a distal edge of the at least one flap is aligned with the proximal end of the at least one divider.

* * * * *